United States Patent
Dang et al.

(10) Patent No.: US 10,882,012 B2
(45) Date of Patent: Jan. 5, 2021

(54) PROCESS FOR PRODUCING A NANO RESVERATROL MICROEMULSION SYSTEM

(71) Applicant: Hong Ngoc Thi Dang, Ho Chi Minh (VN)

(72) Inventors: Hong Ngoc Thi Dang, Ho Chi Minh (VN); Nam Hai Lai, Ho Chi Minh (VN)

(73) Assignee: WAKAMONO CORPORATION, Ho Chi Minh (VN)

( * ) Notice: Subject to any disclaimer, the term of this patent is extended or adjusted under 35 U.S.C. 154(b) by 0 days.

(21) Appl. No.: 16/505,692

(22) Filed: Jul. 8, 2019

(65) Prior Publication Data

US 2019/0336922 A1    Nov. 7, 2019

(30) Foreign Application Priority Data

Aug. 3, 2018   (VN) ............... 1-2018-03407

(51) Int. Cl.
| | | |
|---|---|---|
| B01F 3/08 | (2006.01) | |
| B01F 3/22 | (2006.01) | |
| B01F 3/20 | (2006.01) | |
| A61K 9/51 | (2006.01) | |
| A61K 9/107 | (2006.01) | |
| B82Y 5/00 | (2011.01) | |
| A61K 31/05 | (2006.01) | |

(52) U.S. Cl.
CPC .......... *B01F 3/0811* (2013.01); *A61K 9/1075* (2013.01); *A61K 9/5146* (2013.01); *B01F 3/2078* (2013.01); *B01F 3/2261* (2013.01); *A61K 31/05* (2013.01); *B82Y 5/00* (2013.01)

(58) Field of Classification Search
CPC .... B01F 3/0811; B01F 3/2261; B01F 3/2078; A61K 9/5146; A61K 9/1075; A61K 31/05; B82Y 5/00
See application file for complete search history.

(56) References Cited

U.S. PATENT DOCUMENTS

| 8,465,757 B2 * | 6/2013 | Duan ...................... A61P 9/10 424/401 |
| 8,476,248 B2 * | 7/2013 | Arigony Souto ....... A61P 29/00 514/58 |

FOREIGN PATENT DOCUMENTS

CN    104324020    * 11/2014

* cited by examiner

*Primary Examiner* — Shirley V Gembeh
(74) *Attorney, Agent, or Firm* — BN IP-Consulting LLC; Binh-An Nguyen

(57) ABSTRACT

The present invention relates to a process of producing a nano resveratrol microemulsion system includes: (i) preparing a dispersal phase by dissolving resveratrol in an ethanol solvent; (ii) preparing a carrier by heating a liquid PEG (polyethylene glycol) accounted from 40 to 60% by mass of the mixture of PEG and water to a temperature ranging from 60 to 80° C., then adding zeolite catalyst (0.1-0.4% by mass of mixture of PEG and water), stirring evenly; (iii) adding the carrier to the dispersal phase (in a ratio by mass of 40:60), continuing heating the said dispersal phase to 100° C., stirring at a speed of 400 to 800 rpm; (iv) elmusifying as follows: when the temperature arrives at 100° C., adding Tween to the mixture of the carrier and dispersal phase in step (iii) in a ratio by mass of 40:60, continuing to stir at a speed of 500 to 700 rpm, at a temperature of 100° C. to 130° C. perform emulsification at speed of 2500 to 3500 rpm, combining stirring at a speed of 400 and 600 rpm, in vacuum, the reaction temperature is maintained at 150° C. for 3 to 5 hours, the reation is quenched, the temperature is decreased slowly until it is in the range of 40 to 60° C.; (v) filtrating the product by injecting through nanofilter system before filling-packaging.

3 Claims, 1 Drawing Sheet

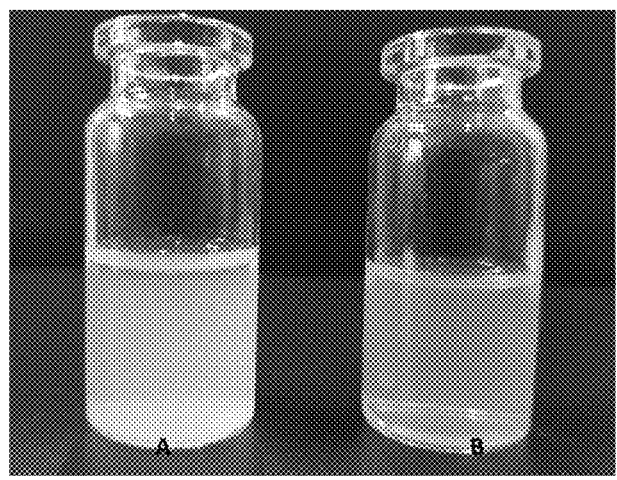

PROCESS FOR PRODUCING A NANO RESVERATROL MICROEMULSION SYSTEM

TECHNICAL FIELD

The present invention relates to a process for producing a nano resveratrol microemulsion system.

BACKGROUND OF THE PRESENT INVENTION

Resveratrol is the ingredient that is abundant in at least about 70 types of plants, including grapes (grape wines), peanuts (peanuts are a daily food containing large resveratrol content, also known as "longevity fruit"), pineapples, strawberries, etc. Resveratrol has a ring structure consisting of many hydroxy, hydroxy can through oxidation to promote antioxidant function, the antioxidant ability is stronger than vitamins C, E, and glutathione.

Resveratrol not only helps reduce blood fat, treat hypertension, but can also inhibit abnormal clotting of platelets (anti-clogged arteries), widen blood vessels, improve microcirculation; helps prevent coronary artery disease, arteriosclerosis disease, helps brain blood vessels to recover smoothly, increases brain working time; increases immune system, antibacterial, viral infection resistance, anti-inflammatory and anti-allergic effects, etc.

Resveratrol is well-absorbed after administered orally, and has high activity in the body but low bioavailability. It is fastly metabolised and therefore the non-degraded resveratrol content in the blood is low. It was discovered mainly as metabolites in blood and urine, the biological activity of these metabolites is also unknown. It dissolves fat, and is found as a form of glucose or glucoside binding, called piceid. Resveratrol is well-absorbed after administered orally, and has high activity in the body but low bioavailability; it is fastly metabolised and therefore the non-degraded resveratrol content in the blood is low, thus, it is very necessary to improve the ability of absorption, increase the bioavailability of the agent. Applying nano technologies is a novel technological application for generating drug vehicle systems and increasing the bioavailability of the agent. When particle sizes are below 100 nm, the ability of absorption and the ability of storage will increase. Resveratrol is encapsulated in a nano drug vehicle systems, the size of the particle is less than 100 nm, thanks to the ability to store nano drug vehicle system, which helps transport the agent to targets in a selectively, effectively and drug-saving way. In our country, nano technologies in biomedical fields remain new and not yet have many applications but have attracted so much interest to study. The most common existing studies are the applications of nanocurumin and drug transporting systems to target cells, there have not been studies to manufacture nano resveratrols. Using nanoparticles to carry and release drugs is a new strategy for treating diseases, specifically cancers in the future.

Anitha Krishnan Nair et al. in US Patent Publication No. 2011/0229532 A1 provided a process for producing a microemulsion system of compounds belonging to an oleophilic polyphenol group by using ultrasonic with non-ionic surfactant and one non-ionic solvent to enhance the water solubility.

Therefore, there is a demand of a process for producing a microemulsion system having micelles with dimensions smaller than 100 nm, uniformity, better water-solubility while retaining the structure, activity of resveratrol in nano-processing.

SUMMARY OF THE PRESENT INVENTION

An object of the present invention is to provide a process for producing a nano resveratrol microemulsion system to produce particles having dimensions smaller than 100 nm, uniformity, ability to dissolve in water while the activity and structure is retained to help increase utility effects of resveratrol active agents, in particular, increase the ability of absorption and increase the bioavailability.

To achieve the above object, the process for producing a nano resveratrol microemulsion system of the present invention includes:

(i) preparing a dispersal phase by dissolving resveratrol in an ethanol solvent in a ratio between mass of resveratrol: volumn of ethanol solvent as 8:10 by a stirrer at a speed of 300 to 500 rpm with heating to a temperature from 40 to 60° C. within 4 to 8 hours;

(ii) preparing a carrier by heating a liquid PEG (polyethylene glycol) accounted from 40 to 60% by mass of the mixture of PEG and water to a temperature ranging from 60 to 80° C., then adding zeolite catalyst in a ratio by mass of 0.1 to 0.4% of mixture of PEG and water, stirring evenly;

(iii) adding the carrier to the dispersal phase in a ratio by mass of 40:60, continuing heating the said dispersal phase to 100° C., stirring at a speed of 400 to 800 rpm;

(iv) emulsifying as follows: when the temperature arrives at 100° C., adding Tween to the mixture of the carrier and dispersal phase in step (iii) in a ratio by mass of 40:60, continuing to stir at a speed of 500 to 700 rpm, at a temperature of 100° C. to 130° C., perform emulsification at speed of 2500 to 3500 rpm, combining stirring at a speed of 400 and 600 rpm in a vacuum, the reaction temperature is maintained at 150° C. for 3 to 5 hours, controlling the quality of resulting products by dissolving into water and measuring the transparency, if it fails then continuing heating and measuring this transparency every 30 minutes until it is observed to be transparent, the reation is quenched, the temperature is decreased slowly until it is in the range of 40 to 60° C.;

(v) filtrating the product by injecting through nanofilter system before filling-packaging.

BRIEF DESCRIPTION OF THE DRAWINGS

FIG. 1 shows a picture comparing the water-dispersing ability between a known 99% resveratrol and the nano resveratrol obtained by the process of the invention.

DETAILED DESCRIPTION OF THE PRESENT INVENTION

The process for producing a nano resveratrol microemulsion system of the present invention is performed as follows:

(i) First step: preparing a dispersal phase by dissolving resveratrol in an ethanol solvent in a ratio between mass of resveratrol:volume of ethanol solvent as 8:10 by a stirrer at a speed of 300 to 500 rpm with heating to a temperature from 40 to 60° C. within 4 to 8 hours.

The inventors used ethanol as a solvent that is capable of dissolving resveratrol well, helps form a better dispersal phase and facilitate this dispersal phase being able to combine better with PEG carrier.

Using hydroxyl (OH—) based-ethanol solvent forms a linkage with water then has effects on stabilizing the structure of the oil-in-water microemulsion system. By experiments, the inventors determined that, in a 8:10 ratio of resveratrol:ethanol (mass:volume), resveratrol achieved the highest solubility and avoided the redundancy of ethanol solvent, which is a wastage.

The use of stirring and heating generates resveratrol dispersing better, when the inventors carried out the experiments under various stirring conditions and temperatures, it was shown that at a speed of 300-500 rpm and simultaneously heating at a temperature ranging from 40 to 60° C., the dispersal phase of resveratrol was better and the combination with PEG carriers was better.

(ii) Second step: preparing a carrier by heating a liquid PEG (polyethylene glycol) accounted for 40 to 60% by mass of the mixture of PEG and water to a temperature ranging from 60 to 80° C., then adding zeolite catalyst in a ratio by mass of 0.1 to 0.4% of mixture of PEG and water, stirring evenly.

When being used, resveratrol is often damaged in the digestive tract, a portion is absorbed into the blood, most of the rest is eliminated. Thus, it needs a process for producing micelles containing resveratrol active agents that have small sizes with bio-coatings, high stable structure, inadherence and high solubility.

Because the microemulsion system of the present invention is employed in food and pharmaceutical industries, the agents selected to use must have high safety, non-toxicity and less side effects.

Many studies have shown that transporting processes of drugs may be improved the effectiveness by vehicle systems derived from kinds of polymers: natural hydrophilic polymers such as protein (gelatine, albumine), polysaccharide (alginate, dextrane, chitosane), synthetic hydrophobic polymer such as polyester (poly (ε-capprolactone), polylactic acid, polylactic-co-glycolic acids. Polymer carriers with relatively high drug loadings can confer many conveniences in pharmacokinetics, namely drugs are kept stably, which can be administered to treat for a long time by the slowly-released process of drugs according to the decomposition of polymer, the biological distribution of drugs, the targeting, the penetration through cell membranes, etc. that can be driven by physicochemical properties of polymer.

(iii) Third step: adding the carrier to the dispersal phase (in a ratio of 40:60), continuing heating the dispersal phase to 100° C., stirring at a speed of 400 to 800 rpm.

(iv) Fourth step: emulsifying as follows: when the temperature arrives at 100° C., adding Tween to the mixture of the carrier and dispersal phase in step (iii) in a ratio by mass of 40:60, continuing to stir at a speed of 500 to 700 rpm, at a temperature of 100° C. to 130° C., perform emulsification at speed of 2500 to 3500 rpm, combining stirring at a speed of 400 to 600 rpm, in vacuum, the reaction temperature is maintained at 150° C. for 3 to 5 hours, controlling the quality of resulting product by dissolving into water and measuring the transparency, if it fails then continuing heating and measuring this transparency every 30 minutes until it is observed to be transparent, the reation is quenched, the temperature is decreased slowly until it is in the range of 40 to 60° C.

By theoretical and experimental studies, the inventors found that to produce nano resveratrol with good water solubility, the emulsion system will be in the form of oil-in-water emulsion. Selecting emulsifier to enhance the durability of the microemulsion system was based on properties of this microemulsion system (in the form of oil-in-water microemulsion system, in the form of water-in-oil microemulsion system, etc.). Thus, the inventors selected Tween as an emulsifier, because Tween is a hydrophilic, non-toxic and highly safe agent. The inventors had to carry out so many studies to determine ratios of PEG:Tween of 40:60 (mass:mass) to generate sustainable polymer chains.

As the emulsifier Tween is a molecule with 2 distinct portions, an oleophylic portion and a hydrophilic portion, it is capable of forming linkage with resveratrol and carrier mixture. The oleophylic portion of Tween forms a linkage with the resveratrol and the hydrophilic portion of Tween forms a linkage with the hydrophilic portion of the mixture of PEG carrier, then create nano resveratrol micelles and protect resveratrol activity well with this structure.

Generating the nano resveratrol microemulsion system by performing emulsions at a rate of 2500 to 3500 rpm, combining stirring at a rate of 400 to 600 rpm in vacuum, the reaction temperature is maintained at 150° C. for 3 to 5 hours.

The microemulsion system obtained by the process of the present invention has pH of 7 to 7.4. With these pH value, micelles exist stably because in this neutral environment the linkage between the resveratrol and the carrier material is kept in dispersing process, while the microemulsion system has pH <7 then this linkage weakens resulting the damage of nano resveratrol particles in the digestive tract.

The nano resveratrol microemulsion system obtained by the process of the present invention having HLB of 13 to 18 is a hydrophilic microemulsion system. The microemulsion system has micelles containing inadherent hydrophilic resveratrol, with particle sizes ranging stably from 30 to 80 nm, then it can easily penetrate via cell membranes to develop the effectiveness and increase the solubility of resveratrol in water, thereby enhance the bioavailability of the agent.

(v) Fifth step: filtrating the product by injecting through nanofilter system before filling-packaging to remove excessive amounts of agents and ensure the uniformity, the stability of solution.

EXAMPLES

Example 1: Production of 100 ml of Nano Resveratrol Microemulsion System

A dispersal phase was prepared by dissolving 8 g of resveratrol in 10 ml of ethanol solvent 96° with a stirrer at a speed of 400 rpm, simultaneously heated to a temperature of 40° C. for 6 hours to form a homogeneous solution.

Preparing a carrier: 70 ml of PEG was heated to 70° C. 0.2 g of zeolite catalyst was added to PEG at 70° C., stirring evenly.

70 ml of mixture of the carrier and zeolite catalyst was added to the above-prepared dispersal phase, this dispersal phase continued to be heating to 100° C., stirred at a speed of 600 rpm.

A homogeneous mixture was prepared by mixing the dispersal phase, a mixture of PEG carrier and emulsifier tween (20 ml) in an emulsifying equipment LSP-500 with a frequency of 20 KHz at a stirring speed of 600 rpm.

At 100° C., continued to be stirring at a speed of 600 rpm, at 130° C. perform emulsification at speed of 3000 rpm, combining stirring at speed of 500 rpm, in vacuum, the reaction temperature is maintained at 150° C. for 4 hours, the quality of resulting product was controlled by dissolving into water and the transparency was measured, if it failed then continuing heating and measuring this transparency every 30 minutes until it was observed to be transparent, the reation was quenched, the temperature was decreased slowly until it was 50° C.

Before filling, the product were injected via nanofilter system for the purpose of removing the excessive amount of resveratrol which did not form micelles, obtained a nano resveratrol microemulsion system which dispersed in water well.

By UV-vis spectrophotometry method, the inventors found that positions of peaks of material resveratrol and the nano resveratrol microemulsion system fitted completely. This showed that the microemulsion system obtained by the process of the present invention retained the structure, activity of resveratrol in nanoprocessing.

UV-vis spectrophotometry method were used to quantify the concentrations of resveratrol in the microemulsion system. The results showed that the concentrations of resveratrol in the nano resveratrol microemulsion system were in the range of about 10%.

Measuring sizes of nano resveratrol particles by a scanning electron microscopy TEM (Transmission Electron Microscopy) demonstrated that particle sizes fluctuating from 40 to 55 nm.

| Sizes (nm, according to TEM) | Sizes (nm, according to DLS) | Zeta potential (mV) | Stability (months) | Water solubility |
|---|---|---|---|---|
| 40-45 | 40-45 | −40 | >12 | Well-water solubility, after solubilized in water, the system stabilized >7 days |

The above results showed that using PEG carrier with ratio of Tween is 40:60, zeolite catalyst gave a microemulsion system with micelles having small dimensions (40 to 55 nm), high stability (>12 months), well-water solubility and after dissolved in water, the system stabilized >7 days.

With the reference to FIG. 1, it shows a picture comparing the water-dispersing ability between a known 99% resveratrol and the nano resveratrol obtained by the process of the present invention, in which bottle A showed the known 99% water-dispersed resveratrol, bottle B showed the water-dispersed nano resveratrol obtained by the process of the present invention.

The picture showed that the known 99% resveratrol was insoluble in water, formed water-suspending particles, a cloudy solution which encrusted at the bottom of bottle over time.

The nano resveratrol obtained by the process of the present invention completely dispersed in water generated a transparent, homogeneous solution.

Advantageous Effects of the Invention

The process for producing a nano resveratrol microemulsion system of the present invention succeeds in manufacturing a microemulsion system having nano resveratrol micelles with small dimensions of 40 to 55 nm, which is uniform and good water-soluble while retains the structure, activity of resveratrol in nanoprocessing.

The agents used in the process for producing nano resveratrol, which disperse well in water, are highly safe, non-toxic and have less side effects, then the nano resveratrol microemulsion system obtained by the process of the present invention has high safety when being used.

The process of the present invention is simple, easy to perform and suitable with current actual conditions in our country.

The invention claimed is:

1. A process for producing a nano resveratrol microemulsion system includes the steps of:
   (i) preparing a dispersal phase by dissolving resveratrol in an ethanol solvent in a ratio between mass of resveratrol:volumne of ethanol solvent as 8:10 by a stirrer at a speed of 300 to 500 rpm with heating to a temperature from 40 to 60° C. within 4 to 8 hours;
   (ii) preparing a carrier by heating a liquid PEG (polyethylene glycol) accounted from 40 to 60% by mass of the mixture of PEG and water to a temperature ranging from 60 to 80° C., then adding zeolite catalyst in a ratio by mass of 0.1 to 0.4% of mixture of PEG and water, stirring evenly;
   (iii) adding the carrier to the dispersal phase in a ratio by mass of 40:60, continuing heating the said dispersal phase to 100° C., stirring at a speed of 400 to 800 rpm;
   (iv) emulsifying as follows: when the temperature arrives at 100° C., adding Tween to the mixture of the carrier and dispersal phase in step (iii) in a ratio by mass of 40:60, continuing to stir at a speed of 500 to 700 rpm, at a temperature of 100° C. to 130° C., perform emulsification at speed of 2500 to 3500 rpm, combining stirring at a speed of 400 and 600 rpm, in vacuum, the reaction temperature is maintained at 150° C. for 3 to 5 hours, controlling the quality of resulting product by dissolving into water and measuring the transparency, if it fails then continuing heating and measuring this transparency every 30 minutes until it is observed to be transparent, the reaction is quenched, the temperature is decreased slowly until it is in the range of 40 to 60° C.;
   (v) filtrating the product by injecting through nanofilter system before filling-packaging.

2. The process of claim 1, wherein the nano resveratrol microemulsion system obtained by the process having micelles containing inadherent hydrophillic resveratrol, with particle sizes ranging stably from 30 to 80 nm.

3. The process of claim 1, wherein the nano resveratrol microemulsion system obtained by the process having concentrations of resveratrol in a range of about 10%.

* * * * *